United States Patent
Rogers

(10) Patent No.: US 10,492,861 B2
(45) Date of Patent: Dec. 3, 2019

(54) METHOD AND APPARATUS FOR TREATING SOFT TISSUE INJURY

(71) Applicant: Mark John McDonald Rogers, Parkside (AU)

(72) Inventor: Mark John McDonald Rogers, Parkside (AU)

( * ) Notice: Subject to any disclaimer, the term of this patent is extended or adjusted under 35 U.S.C. 154(b) by 14 days.

(21) Appl. No.: 15/563,012

(22) PCT Filed: Apr. 4, 2016

(86) PCT No.: PCT/AU2016/000112
§ 371 (c)(1),
(2) Date: Sep. 29, 2017

(87) PCT Pub. No.: WO2016/154664
PCT Pub. Date: Oct. 6, 2016

(65) Prior Publication Data
US 2018/0250072 A1   Sep. 6, 2018

(30) Foreign Application Priority Data
Apr. 2, 2015   (AU) ................. 2015901207

(51) Int. Cl.
*A61B 18/20*   (2006.01)
*A61N 5/06*   (2006.01)
(Continued)

(52) U.S. Cl.
CPC ........... *A61B 18/20* (2013.01); *A61B 5/0059* (2013.01); *A61B 5/015* (2013.01); *A61N 5/0625* (2013.01);
(Continued)

(58) Field of Classification Search
CPC ...... A61N 5/00; A61N 5/0613; A61N 5/0616; A61N 5/1048; A61N 5/1064;
(Continued)

(56) References Cited

U.S. PATENT DOCUMENTS

| 4,524,778 A | 6/1985 | Brown et al. |
| 5,370,114 A | 12/1994 | Wong et al. |

(Continued)

FOREIGN PATENT DOCUMENTS

| FR | 2561515 | 9/1985 |
| RU | 2160039 | 12/2000 |

(Continued)

OTHER PUBLICATIONS

International Search Report and Written Opinion prepared by the Australian Patent Office on Jun. 15, 2016, for International Application No. PCT/AU2016/000112.

(Continued)

*Primary Examiner* — Allen Porter
(74) *Attorney, Agent, or Firm* — Sheridan Ross PC

(57) ABSTRACT

An apparatus for the treatment of a soft tissue injury (eg a soft tissue injury that may be the cause, or contributes to, acute or chronic pain such. as sciatica) comprising; a thermal imaging arrangement to scan, a least a portion of a patient to provide a thermal image; a processing arrangement to review the thermal image to determine a point or region of thermal anomaly on the patient; a laser treatment device to provide a laser beam (eg for low-level laser treatment); and a guidance arrangement for the laser treatment device to guide the laser beam to the point or region of thermal anomaly on the patient as determined by the processing arrangement; to thereby treat the patient.

13 Claims, 3 Drawing Sheets

(51) Int. Cl.
  *A61B 5/01* (2006.01)
  *A61B 5/00* (2006.01)
  A61B 18/00 (2006.01)
  A61B 18/22 (2006.01)
  A61N 5/067 (2006.01)

(52) U.S. Cl.
  CPC .............. *A61B 2018/00642* (2013.01); *A61B 2018/00708* (2013.01); *A61B 2018/00809* (2013.01); *A61B 2018/2283* (2013.01); *A61N 5/06* (2013.01); *A61N 2005/067* (2013.01); *A61N 2005/0659* (2013.01)

(58) Field of Classification Search
  CPC .... A61N 5/1067; A61N 5/1069; A61N 5/107; A61N 5/1077; A61N 5/1083; A61N 2005/0635; A61N 2005/0636; A61N 2005/0637; A61N 2005/0638; A61N 2005/0642; A61N 2005/0643; A61N 2005/1054; A61N 2005/1059
  See application file for complete search history.

(56) References Cited

U.S. PATENT DOCUMENTS

| | | |
|---|---|---|
| 5,865,167 A | 2/1999 | Godik |
| 5,951,596 A * | 9/1999 | Bellinger ................ A01M 1/02 606/9 |
| 6,272,936 B1 | 8/2001 | Oreper et al. |
| 6,397,099 B1 | 5/2002 | Chance |
| 6,929,607 B2 | 8/2005 | Lipman |
| 6,934,576 B2 | 8/2005 | Camacho et al. |
| 7,477,767 B2 | 1/2009 | Chhibber et al. |
| 2002/0010400 A1 | 1/2002 | Camacho et al. |
| 2002/0099293 A1 | 7/2002 | Fontenot et al. |
| 2004/0008523 A1 * | 1/2004 | Butler ................. A61N 5/0613 362/551 |
| 2004/0019269 A1 | 1/2004 | Schaefer et al. |
| 2004/0019303 A1 | 1/2004 | Thomson |
| 2006/0111622 A1 | 5/2006 | Merritt et al. |
| 2008/0255429 A1 | 10/2008 | Centeno |
| 2008/0269847 A1 | 10/2008 | Nemenov |
| 2009/0105588 A1 | 4/2009 | Emelianov et al. |
| 2010/0049180 A1 * | 2/2010 | Wells ................. A61N 5/0616 606/12 |
| 2011/0184284 A1 | 7/2011 | McKay |
| 2011/0230942 A1 | 9/2011 | Herman et al. |
| 2013/0204158 A1 | 8/2013 | Rogers |
| 2014/0303608 A1 | 10/2014 | Taghizadeh |

FOREIGN PATENT DOCUMENTS

| | | |
|---|---|---|
| WO | WO 2006/012752 | 2/2006 |
| WO | WO 2015/179187 | 11/2015 |
| WO | WO 2016/154664 A1 | 10/2016 |

OTHER PUBLICATIONS

International Preliminary Report on Patentability by the Australian Patent Office on Jul. 26, 2016, for International Application No. PCT/AU2016/000112.

Extended Search Report for European Patent Application No. 16771085.4, dated Oct. 24, 2018, 7 pages.

Liebert et al., "Protein conformational modulation by photons: A mechanism for laser treatment effects," Medical Hypothesis, 2014, vol. 82(3), pp. 275-281.

\* cited by examiner

METHOD AND APPARATUS FOR TREATING SOFT TISSUE INJURY

CROSS REFERENCE TO RELATED APPLICATIONS

This application is a national stage application under 35 U.S.C. 371 and claims the benefit of PCT Application No. PCT/AU2016/000112 having an international filing date of 4 Apr. 2015, which designated the United States, which PCT application claimed the benefit of Australian Patent Application No. 2015901207 filed 2 Apr. 2015, the disclosure of each of which are incorporated herein by reference.

TECHNICAL FIELD

The present invention relates to the treatment of injury, particularly a soft tissue injury, which may be the cause, or contributes to, acute or chronic pain, including chronic referred pain known such as sciatica.

PRIORITY DOCUMENT

The present application claims priority from Australian Provisional Patent Application No 2015901207 titled "Method and apparatus for treating soft tissue injury" filed on 2 Apr. 2015, the content of which is hereby incorporated by reference in its entirety.

INCORPORATION BY REFERENCE

The following co-pending patent application is referred to in the following description: International Patent Application No PCT/AU2011/000609 (WO 2011/146969) titled "Method of diagnosis and location of a soft tissue injury" filed on 23 May 2011. The content of this application is hereby incorporated by reference in its entirety.

BACKGROUND

Soft tissue injuries are identified as a major source of pain and disability and occur across a wide section of the community. Generally, soft tissue injuries arise as a result of damage to muscles, nerves, connective tissues, fascia, joint capsules, periosteum etc as a result of excessive force/stress in a given moment, or repetitive strain placed upon these tissues over an extended period of time. As such, soft tissue injuries are very common in the work-place. Additionally, soft tissue injuries can occur as a result of trauma (eg resulting from sporting incidents and motor vehicle accidents); these injuries may not always be immediately obvious at the time of the trauma, but can become the cause of significant chronic pain at a later date.

Soft tissue injuries can be considered to comprise one or more fracture(s), because it involves the local separation of tissue (eg muscle, tendon or ligament tissue) into two or more pieces under the action of stress. Hence, damage to soft tissue can be interchangeably referred to as a "soft tissue stress fracture" or "soft tissue injury". Commonly, the size of the fracture(s) may be relatively large (eg a tear of 0.5 to 3.0 cm), but in many instances, the fracture(s) may be of the microscopic scale (eg a tear of ≤2.0 mm, such as a tear of about 1.0, 0.5 or 0.2 mm, which may comprise one or more individual tissue fracture such as one or more fractures within collagen tissue). Nevertheless, both large and microscopic soft tissue injuries can lead to significant acute and/or chronic pain. At least in part, the pain is due to the body's inflammatory response to the injury. That response results from a complex cascade of events that includes changes to the concentration of various chemical components within the body, such as histamines, prostaglandins, cytokines etc along with the stimulation and/or proliferation of various inflammatory cells such as leukocytes, fibroblasts and macrophages, and can lead to a range of physiological effects mediated by an increase in inflammatory hormones and/or nerve chemicals at the site of injury. Such physiological effects may include swelling, hypersensitivity, neuritis, fasciculation, involuntary muscle contraction, heat, reduced blood flow and, critically, a reduced ability of the lymphatic system to drain interstitial fluid (lymphoedema). All of this can lead to a vicious cycle of pain for the patient.

Effectively treating pain arising from a soft tissue injury requires identification of the site of injury. This can be difficult since the region of the body where the patient perceives the pain to be present can be at some distance or even quite remote (ie referred pain) to the location of the causative soft tissue injury. Moreover, given their small size, soft tissue injuries can quite simply be very difficult to diagnose or pinpoint, especially with the lapse of time.

One approach to the detection of small tissue injuries is to use Magnetic Resonance Imaging (MRI). However, such equipment requires a detailed understanding of the symptoms of the injured person, his/her case history, and then, based on that information, very precise and localised use of the equipment to observe the injury. Moreover, the equipment used for this form of imagery is very expensive and cannot, therefore, be used on a day-to-day basis by general medical practitioners (GPs). Consequently, the use of MRI is not regarded as a practical or useful tool for the general diagnosis of soft tissue injuries.

An alternative approach is to look for and detect the inflammatory response at and around the site of a soft tissue injury. In his previous patent application, PCT/AU2011/000609 supra, the present inventor has described certain methods based upon this approach. In brief, such methods can involve initially obtaining a thermographic image (thermal image) of an area suspected of being associated with the patient's pain to enable visualisation of variation in surface temperature using an infrared imaging camera. This involves resolving the thermal image to reveal a "hot" area typically no more than about 2-5 cm in length or diameter that may point towards the region of inflammation (ie causing heat). However, since it can be difficult for a medical practitioner or therapist to match the hot area as indicated on the thermal image to the exact site on the patient's body and/or pinpoint the site of injury within the location corresponding to the hot area, it has proven insufficient to provide a reliable diagnosis or pinpointing of the site of injury based upon a thermal image alone. Accordingly, the methods described in PCT/AU2011/000609 further involve the application of electromagnetic (EM) energy or radiation to the location corresponding to the hot area through the use of, for example, a laser probe and thereafter obtaining the patient's feedback on the level of a warming sensation caused by the EM energy or radiation at each region or point of application. The site of the soft tissue injury corresponds to the region or point(s) where the sensation is warmest but not uncomfortable (eg a sensation rating of 6-8 on a scale of 1 to 10). Once the site of soft tissue injury has been identified in this way, the methods enable effective treatment through, for example, the further application of EM energy or radiation of suitable wavelength and intensity (eg "cold" laser therapy, otherwise known as low-level laser treatment (LLLT) and photobiomodulation (PBMT), known to be effective in the treatment of chronic pain such as that caused by chronic inflammatory conditions, wound repair and lymphoedema; Liebert A D et al., *Medical Hypothesis* 82(3): 275-281, 2014) by a medical practitioner or therapist to the identified site of soft tissue injury.

While the methods described in PCT/AU2011/000609 have proven to be highly effective in detecting and thereby enabling the effective treatment of soft tissue injury, there is a desire to provide an improved methodology which is less operator-dependent and/or less reliant on verbal feedback from the patient being treated. The present invention is therefore directed at providing a novel method and apparatus for treating soft tissue injury which may address one or both of these issues.

SUMMARY

According to a first aspect, there is provided an apparatus for the treatment of a soft tissue injury comprising:

a thermal imaging arrangement to scan at least a portion of a patient to provide a thermal image;

a processing arrangement to review the thermal image to determine a point or region of thermal anomaly on the patient;

a laser treatment device to provide a laser beam; and a guidance arrangement for the laser treatment device to guide the laser beam to the point or region of thermal anomaly on the patient as determined by the processing arrangement, to thereby treat the patient.

The apparatus is suitable for the treatment of a macroscopic or microscopic scale soft tissue injury occurring in one or more of soft tissue such as a muscle, tendon, ligament, fascia, nerve, fibrous tissue, adipose tissue (fat), blood vessel and synovial membranes.

The apparatus preferably comprises a bed to support the patient.

In apparatus comprising a bed, the guidance arrangement moves the laser treatment device with respect to the bed and/or moves the bed with respect to the laser treatment device. Further, such apparatus may comprise a first movement arrangement to move the thermal imaging arrangement with respect to the bed and/or to move the bed with respect to the thermal imaging arrangement. Moreover, in such apparatus, both the thermal imaging arrangement and the laser treatment device are mounted on a single arm which is moveable with respect to the bed or in which the bed is moveable with respect to the single arm or both the bed and the single arm are moveable with respect to each other. Alternatively, the thermal imaging arrangement and the laser treatment device are mounted on separate arms each of which can move with respect to the bed. The bed can be arranged to support the patient in a vertical, prone or semi-prone position. The bed may be contained within a pod (akin to typical sun beds) with a hinged or pivotably mounted cover or privacy screen to enable the pod to be opened and closed to allow ingress and egress of the patient, or otherwise, the bed may be provided with a cover that may be similarly hinged or pivotably mounted or, in an embodiment, is simply fixed at a distance above the bed that allows the patient to readily move onto and off the bed. The thermal imaging device, laser treatment device and all or part of the guidance arrangement may be mounted onto the cover or screen. The apparatus may also be fixed to the ceiling with a bed positioned underneath.

The thermal imaging arrangement may be selected from infrared medical imaging cameras well known to those skilled in the art.

Preferably, the thermal imaging arrangement provides a digital thermal image, preferably an image of at least 12500) pixels, more preferably at least 1900 pixels (eg a 160×120 pixel array image; 19200 pixels), and even more preferably at least 50000 pixels. Most preferably, the thermal imaging arrangement provides a digital thermal image of at least 75000 pixels such as a 320×240 pixel image (76800 pixels) or a 640×480 pixel image (307200 pixels), which may or may not be interpolated images generated using well known interpolation techniques.

Preferably, the thermal imaging arrangement provides a digital thermal image based upon temperature sensitivity of ≤0.1° C. (at 30° C.) and, more preferably, ≤0.05° C. (at 30° C.), or at least 40 mk (at 30° C.), more preferably at least 50 mk (at 30° C.) and, more preferably, at least 100 mk (at 30° C.).

The processing arrangement reviews the thermal image to determine a point or region of thermal anomaly on the patient. Such a point or region on the patient preferably corresponds or resides within a hot spot(s) (ie a point of greatest surface temperature on the area of the body shown in the thermal image); in a typical thermal image, this will be indicated by white colour and will represent a surface temperature that is no more than about 0.5° C. warmer than the immediately surrounding area(s), which will typically be indicated in red. The determination of the point or region by the processing arrangement may involve resolving the thermal image to reveal a hot spot(s) on the patient's body of ≤5.0 cm in length or diameter, but more preferably such that hot spot(s) is ≤2.0 mm in length or diameter such that the hot spot(s) is of a microscopic size corresponding with the location of a microscopic soft tissue fracture (eg a hot spot on the patient's body of about 1.0, 0.5 or 0.2 mm in length or diameter). In any case, the processing arrangement of the apparatus preferably reviews the thermal image to determine a point or region of thermal anomaly on the patient image to reveal a hot spot(s) on the patient's body of ≤5.0 cm in length or diameter, but more preferably such that hot spot(s) is ≤2.0 mm in length or diameter.

The laser treatment device preferably provides laser treatment radiation at a selected wavelength or a set of wavelengths in the range of 400 nm to 10,000 nm (which corresponds to the visible, near-infrared and infrared wavelength spectrums). More preferably, the laser treatment device provides laser treatment radiation at a wavelength in the range of 800 nm to 900 nm (eg 808 nm, 830 nm or 850 nm). The laser treatment device may provide (eg emit) one or more laser beams. Suitable laser treatment devices are well known to those skilled in the art. Such laser treatment devices preferably provide "cold" laser therapy (photobiomodulation, PBMT) known to be effective in the treatment of chronic pain such as that caused by chronic inflammatory conditions, wound repair and lymphoedema. One particular example of a suitable laser treatment device comprises two 300 mW 830 nm infrared laser beams.

The guidance arrangement comprises means to direct the laser beam(s) at a selected angle and/or a selected distance with respect to the patient.

Preferably, the guidance arrangement comprises means to bring the laser treatment device into contact with the skin of the patient (ie at a point or region of thermal anomaly), such that the laser beam is directed immediately at the skin surface (ie there is practically no distance between the laser beam source or beam-focussing optics (eg collimating lens) and the skin surface). In such embodiments, the laser treatment device may be contacted with the skin such that it causes blanching (ie a whitish appearance caused by the prevention/reduction of blood flow to the site). A force sensor (eg a thin-film FlexiForce™ sensor; Tekscan, Inc., South Boston, Mass., United States of America, as described in U.S. Pat. No. 5,272,936) may be provided on part or all of a surface of the laser treatment device that contacts the skin to determine a force (ie pressure) at which skin blanching would typically be expected. Once that force is reached, the guidance arrangement may halt further movement of the means that brings the laser treatment device into skin contact. In another embodiment, a photosensor can be used to measure the colour of the skin as pressure is applied. In other embodiments, an oximeter may be used to determine the point at which movement of the laser treatment device should be halted.

In some embodiments, the apparatus further comprises a timing arrangement which prevents the laser beam from being directed to a single point on the patient for more than about 5-8 minutes, more preferably for no more than about 6 minutes. The timing arrangement preferably comprises a timing device such as a clock or timer. The timing arrangement may operate with the guidance arrangement to direct the laser beam(s) at a single point on the patient for a period in the range of 3-8 minutes, more preferably in the range of 3-6 minutes. The single point on the patient preferably corresponds or resides within a hot spot(s) (ie a point of greatest surface temperature on the region of the body shown in the thermal image); which, in a typical thermal image, will be indicated by white colour and represents a surface temperature that is no more than about 0.5° C. warmer than the surrounding region(s). After treatment at that single point (ie a first point), the timing arrangement may operate with the guidance arrangement to direct the laser beam(s) to a second point on the patient for a period in the range of 3-8 minutes; this second point may preferably correspond to a surrounding and/or adjacent spot(s) that is slightly cooler (eg <1° C., preferably about 0.5° C., cooler than the hot spot(s)) which, in a typical thermal image, will be indicated by red colour, the second point may represent a site of lymphoedema to be treated. After the second period, the laser beam(s) may be re-directed to the first point or to, for example, a third point corresponding to another hot spot(s). After any or each cycle of application of the laser beam(s) (eg after directing the laser beam(s) to said first point, and then optionally after, the laser beam(s) has been directed to said second point, etc), the thermal imaging arrangement may again scan the relevant portion of the patient to provide a new thermal image, which may then be reviewed to assess/monitor the outcome of the laser beam(s) application(s) and/or, through review by the processing arrangement, to determine a further point or region of thermal anomaly on the patient at which to direct the laser beam(s) through operation of the guidance arrangement.

According to a second aspect, there is provided a method of treating a soft tissue injury in a patient, comprising subjecting the patient to treatment with the apparatus of the first aspect.

The soft tissue injury may be of the macroscopic or microscopic scale and may occur in one or more soft tissues such as those mentioned above. The soft tissue injury may be causative, or at least contribute to, acute or chronic pain, including chronic referred pain (eg sciatica) and migraine.

One particular application provides a method of treating a soft tissue injury that is the cause, or contributes to, chronic lower back pain. It has been found that while lower back pain is usually suffered as a large, broadband region of pain, the actual site of the initial and often re-occurring injury is a microscopic soft tissue tear or strain. The method of the invention enables laser treatment to be accurately and effectively applied to the point(s) or region of thermal anomaly on the back of the patient corresponding to inflammation associated with the injury (eg inflammation at the site of the injury). Some assistance or "clue" as to where to initially "point" the thermal imaging arrangement of the apparatus (to obtain a thermal image revealing the point(s) or region of thermal anomaly) may be obtained by interviewing the patient prior to treatment in respect of the injury's history and possible causative event (eg sporting or gardening accident).

Another particular application provides a method of treating a soft tissue injury that is the cause, or contributes to, chronic neck pain. Similarly, it has been found that while neck pain is usually suffered as a large, broadband region of pain, the actual site of the initial and often re-occurring injury is a microscopic soft tissue tear or strain. The method of the invention enables laser treatment to be accurately and effectively applied to the point(s) or region of thermal anomaly on the neck of the patient corresponding to inflammation associated with the injury (eg inflammation at the site of the injury). Some assistance as to where to initially "point" the thermal imaging arrangement of the apparatus may be obtained by interviewing the patient prior to treatment in respect of the injury's history and possible causative event (eg sporting or motor vehicle accident).

Yet another particular application provides a method of treating a soft tissue injury that is the cause, or contributes to, migraine. Studies of migraines have found that they are caused by referred nerve pain that is commonly the result of a long-standing, chronic soft tissue injury at the base of the patient's skull. This injury may have been caused by a childhood fall or a long-forgotten sporting or motor vehicle accident. The method of the invention enables laser treatment to be accurately and effectively applied to the point(s) or region of thermal anomaly on the neck of the patient corresponding to inflammation associated with the injury (eg inflammation at the site of the injury).

The method of the present invention may also be suitable for treating a soft tissue injury that is the cause, or contributes to, tennis elbow, tendinitis, tinnitus, carpal tunnel syndrome or fibromyalgia.

BRIEF DESCRIPTION OF DRAWINGS

Embodiments of the present invention will be hereinafter discussed with reference to the accompanying drawings wherein.

In the following description, like reference characters designate like or corresponding parts throughout the figures.

DETAILED DESCRIPTION

Figure 1:
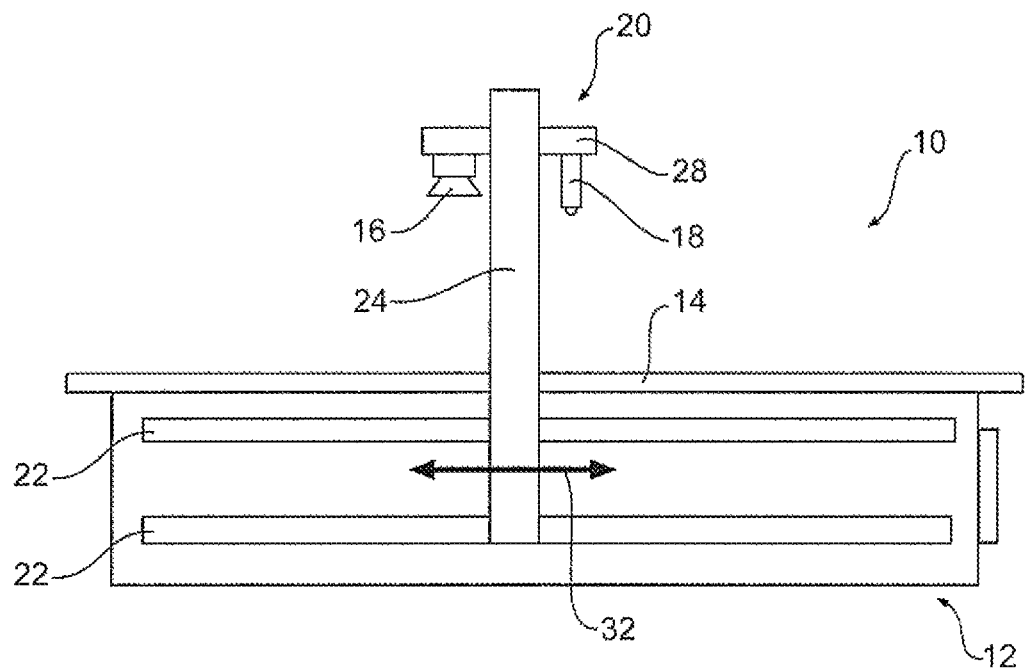
FIG. 1 shows a side view of an apparatus according to one embodiment of the present invention.
Figure 2:
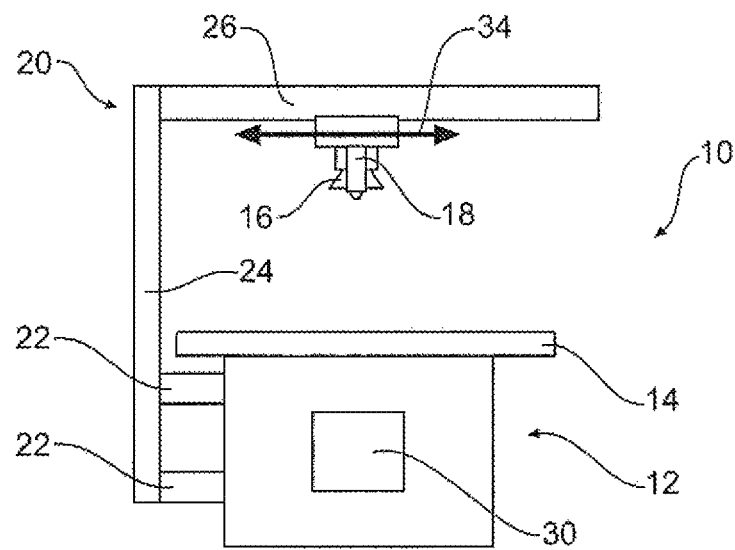
FIG. 2 shows an end view of the apparatus shown in FIG. 1.

Referring now to FIGS. 1 and 2, there is shown an apparatus 10 for the treatment of soft tissue injuries according to a first embodiment of the present invention. In this embodiment, the apparatus 10 includes a bed 12 upon which a patient can lie including an upper surface 14 to support the patient. For the purposes of describing this embodiment, it is assumed that the patient has a soft tissue injury for which the patient lies prone on the surface 14. Pillows and other forms of support (not shown) may be provided on the bed to hold the patient in a selected position.

It will be appreciated that in other embodiments, the apparatus 10 need not include a bed 12 but may be used in association with a separate bed. In such embodiments, the apparatus 10 includes the thermal imaging arrangement 16, the processing arrangement 30, the laser treatment device 18 and the guidance arrangement 28.

The apparatus 10 for treatment of a soft tissue injury has a thermal imaging arrangement 16 which is used to scan a least a portion of the patient to provide a thermal image and a laser treatment device 18 to provide a laser beam to provide appropriate treatment. The thermal imaging arrangement 16 may be selected from infrared imaging cameras well known to those skilled in the art (eg Flir® Max 76 (Flir Systems AB, Täby, Sweden), and Meditherm med2000™ IRIS (Meditherm Inc, Fort Myers, Fla., United States of America)). The laser treatment device 18 may be selected from suitable laser probes, which may emit one or more beams, well known to those skilled in the art. Particular examples of suitable cold laser probes include Maestro Laser Therapy System (MediCom Inc, Prague, Czech Republic), and the Weberneedle Combi-Laser System (Weber Medical GmbH, Sohnreystrasse, Germany)).

In this embodiment, both the thermal imaging arrangement 16 and the laser treatment device 18 are mounted on a single arm 20 which moves longitudinally on a rail arrangement 22 as shown by the arrow 32 with respect to the length of the bed. The arm 20 has an essentially vertical portion 24 and a transverse portion 26 which extends over the bed. Both the thermal imaging arrangement 16 and the laser treatment device 18 are mounted on a housing 28 which is fixed to and moves transversely on the transverse portion 26 of the arm 20 as shown by the arrow 34 in FIG. 2.

The arm 20 can be moved longitudinally along the bed 22 and the housing 28 moved transversely to generally centre the thermal imaging device over the region of the soft tissue injury. Alternatively, where the general region of soft tissue injury may be less clear then the thermal imaging arrangement can be scanned across and along the patient to find regions of thermal anomaly. This scanning across and along can be done automatically by the apparatus of the present invention or by indirect control by an operator who may define a general area of interest such as the shoulders, neck or lower back.

The vertical portion 24 may be able to be raised or lowered relative to surface 14.

In other embodiments, the housing 28, or the individual laser treatment device 18 or thermal imaging arrangement 16, may be raised or lowered along vertical portion 24.

It will be appreciated that in some embodiments, a thermal image as such is not created, but rather simply a dataset, which contains colour information associated with location. This dataset can then be processed directly to provide the guidance information for the guidance arrangement 18.

In such an embodiment, the thermal imaging arrangement may be used, or can be replaced by a thermal scanner which does not necessarily generate an actual image, but rather the dataset.

In such an embodiment, the apparatus 10 will include a thermal scanner for scanning at least a portion of the patient to provide a thermal dataset, a processing arrangement to review the thermal dataset to determine a point or region of thermal anomaly on the patient; a laser treatment device to provide a laser beam, and a guidance arrangement for the laser treatment device to guide the laser beam to the point or region of thermal anomaly on the patient as determined by the processing arrangement, to thereby treat the patient.

A processing arrangement 30 takes information obtained by the thermal imaging arrangement 16 and reviews the thermal image to determine a point(s) or region of thermal anomaly on the patient. As previously described, the single point on the patient preferably corresponds or resides within a hot spot(s) (ie a point of greatest surface temperature on the region of the body shown in the thermographic image); in a typical thermal image, this will be indicated by white colour and will represent a surface temperature that is no more than about 0.5° C. warmer than the immediately surrounding region(s). Such hot spot(s) will typically be no more than about 5.0 cm in length or diameter, and more preferably, no more than about 2.0 mm in length or diameter (eg a hot spot on the patient's body of about 1.0, 0.5 or 0.2 mm in length or diameter) A second point for treatment may be identified by a surrounding and/or adjacent spot(s) that is slightly cooler (eg <1° C., preferably about 0.5° C., cooler than the hot spot(s)) which, in a typical thermal image, will be indicated by red colour.

In the case where a thermal data set is generated in place of or as well as an actual image, corresponding guidance information for use by the guidance arrangement is generated from the dataset indicating where the different thermal regions are located.

The information on the point(s) or region of thermal anomaly on the patient is then transferred to a guidance arrangement for the laser treatment device 18 to guide the laser beam(s) to the point(s) or region of thermal anomaly on the patient as determined by the processing arrangement, to thereby treat the patient. In this illustrative embodiment, the guidance arrangement operates to move the laser treatment device 18 to the region or point(s) by, in this example, having arm 30 scanning or traversing across and along the patient to the region or point(s) of thermal anomaly on the patient to direct the laser beam(s) at a selected angle and/or a selected distance with respect to the patient. In another embodiment, the laser treatment device 18 may be located generally stationary with respect to the patient and an associated directing and/or focusing mechanism operates to direct the laser beam(s) to the region or point(s) of thermal anomaly. In one particular example, the directing mechanism may be a servo or actuator arrangement operating to directly manipulate the laser treatment device 18 to the correct orientation so that the laser beam(s) is directed to the desired location. Additionally or alternatively, the guidance arrangement may comprise a servo or drive arrangement to lower the vertical portion 24 relative to the bed such that the laser treatment device 18 is moved towards, and in some embodiments to contact, the skin of the patient. In another example, the laser treatment device 18 may be statically mounted and guidance of the laser beam(s) achieved by a mirror arrangement controllable to direct the laser beam(s) to the desired location. A timing device associated with the processing arrangement 30 is used to determine a suitable treatment time and then the laser beam(s) is switched on and off in accordance with the treatment time.

It can be seen that by this arrangement, the process of determining a treatment point(s) or region and then applying cold laser treatment to that point(s) or region is essentially automated.

Figure 3:
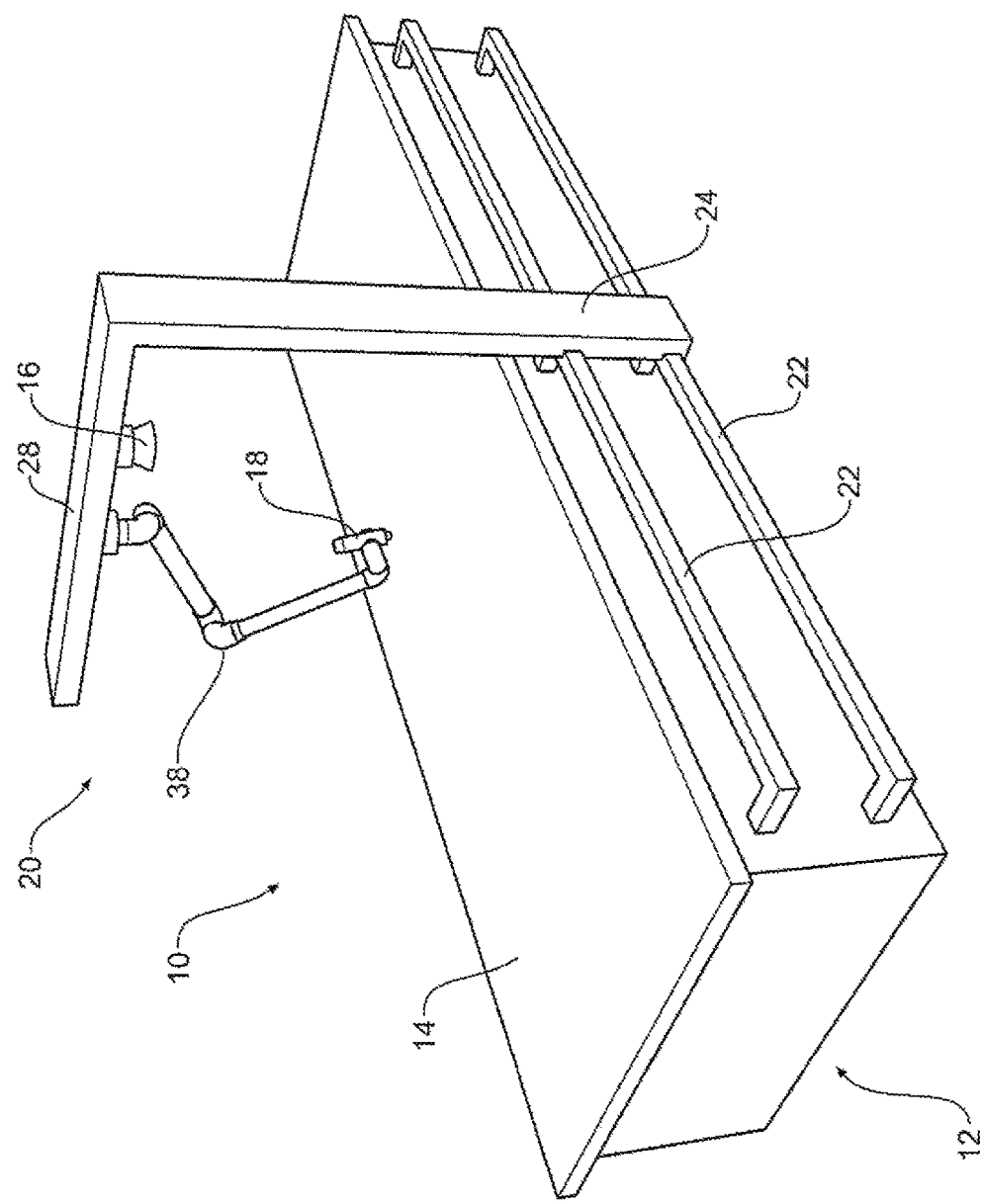
FIG. 3 shows a perspective view of an alternative embodiment of the apparatus shown in FIG. 1.

FIG. 3 shows an end view of an alternative embodiment of the apparatus shown in FIG. 1 wherein the laser treatment device 18 is provided on an orientable arm 38 mounted to housing 28. The particular orientable arm illustrated is a 4 axis robotic universal arm, however those skilled in the art will understand that alternative arms with a fewer or more axis points may also be suitable. Suitable universal robotic arms include those available from Universal Robots A/S (Odense, Denmark).

Figure 4:
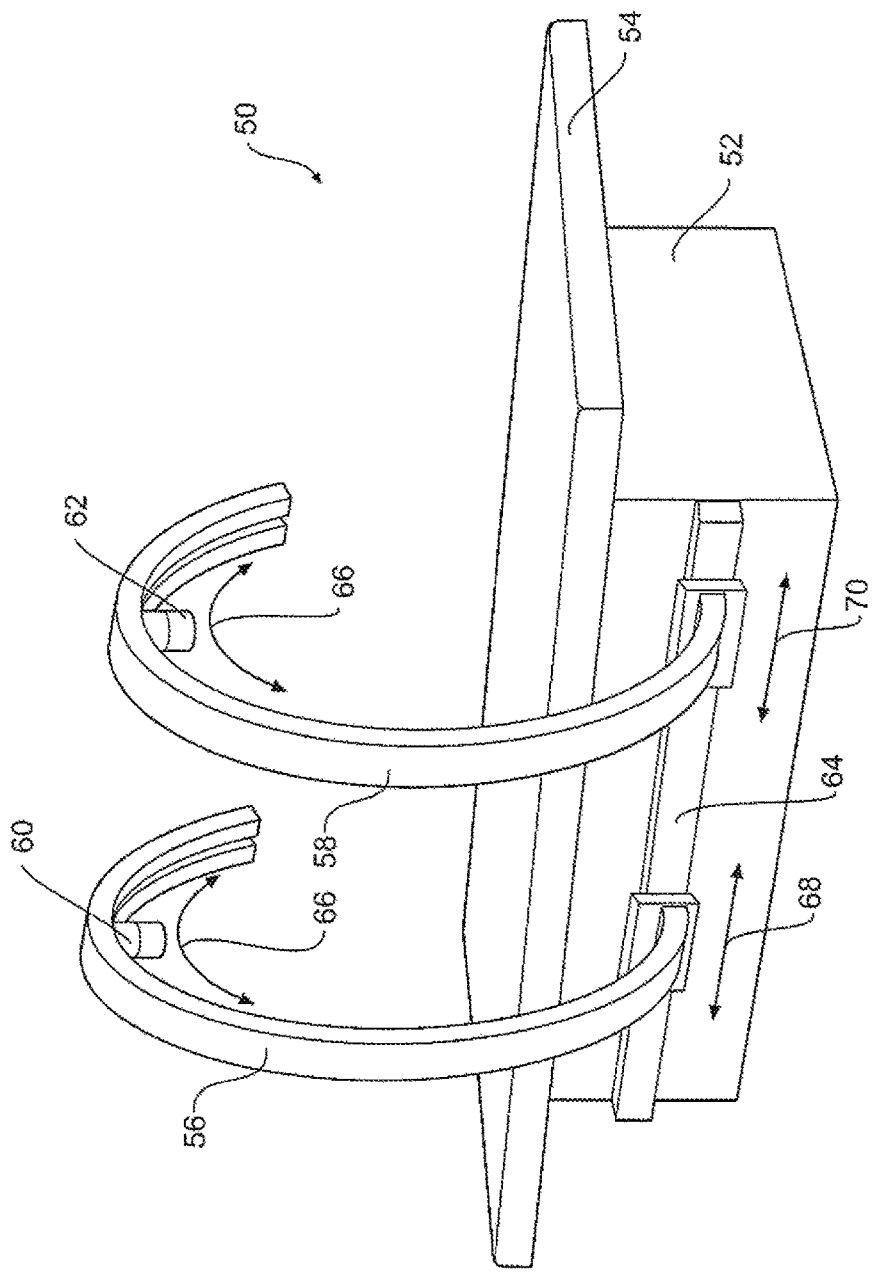
FIG. 4 shows a perspective view of an alternative embodiment of the present invention.

FIG. 4 shows a perspective view of an alternative embodiment of the present invention being an apparatus for the treatment of soft tissue injury. In this embodiment, the apparatus 50 includes a bed 52 (however, in other embodiments, the bed may not be included in the apparatus) upon which a patient can lie including an upper surface 54 to support the patient. For the purposes of describing this embodiment it is assumed that the patient has a soft tissue injury for which the patient lies prone on the surface 54. Pillows and other forms of support (not shown) may be provided on the bed to hold the patient in a selected position.

Over the bed 52 extend, from one side, two semicircular arms 56 and 58. The arm 56 is a detection arm and carries a thermal imaging device 60 such as an infrared imaging camera and the arm 58 is a treatment arm and carries a laser treatment device 62. Each of the arms 56, 58 is supported independently on a track 64 on the side of the bed 52 and each can move longitudinally along the track 64 as shown by the arrows 68, 70. Each of the thermal imaging device 60 and the laser treatment device 62 can move along the inner circumference of the semicircular arms as shown by the arrows 66 so that they can independently view and provide treatment to the patient.

In use, the treatment arm 58 can be moved to one end of the track 64 so that the detection arm 56 can move along the patient to locate a point(s) or region to be treated and then the detection arm 56 can be moved to one end of the track 64 so that the treatment arm 58 can move along the patient to enable the laser beam to be directed to the desired point(s) or region.

From the thermal image or thermal dataset, a location for directing the laser beam may be determined. In one embodiment, a reference grid may be provided over the image which is shared with the guidance arrangement, with the location of the determined point or region of thermal anomaly identified on the grid for use by the guidance arrangement.

In alternative embodiments, the arms can be on opposite sides of the apparatus and be constructed so as not to interfere with the other arm traversing along the full length of a patient.

In some cases, it may be preferable to treat a patient while the patient is standing up and the bed can then be essentially vertical to provide a fixed surface for a patient to be positioned against and both the thermal imaging arrangement and the laser treatment device can be appropriately positioned to scan and treat a selected point(s) or region on the patient. The patient should remain still (ie in the same position) after scanning by the thermal imaging arrangement to optimise the subsequent direction of the laser beam(s).

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

What is claimed is:

1. An apparatus for the treatment of a soft tissue injury including associated inflammation, comprising:
   a thermal imaging camera to scan at least a portion of a patient to provide a thermal image;
   a processor operable to receive information from the thermal imaging camera and to review the thermal image to determine a point or region of thermal anomaly on the patient;
   a laser treatment device to provide a laser beam, wherein the laser treatment device provides laser treatment radiation at a wavelength in the range of 800 nm to 900 nm; and
   a guidance arrangement comprising a servomechanism operable to move the laser treatment device and to direct the laser beam to a desired location, and wherein the guidance arrangement comprises a universal arm operably attached to the laser treatment device to guide the laser beam to the point or region of thermal anomaly on the patient as determined by the processing arrangement, to thereby treat the patient; and
   wherein guidance of the laser beam to the point or region of thermal anomaly comprises providing the laser treatment device into contact with the skin of the patient at a force causing skin blanching; and
   wherein the laser treatment device comprises a force sensor, photosensor or oximeter to generate and provide a signal to the processor when skin blanching has been detected and to cause the processor to halt the guidance arrangement from further movement of the laser treatment device towards the patient once skin blanching has been caused.

2. The apparatus of claim 1, further comprising a bed to support the patient.

3. The apparatus of claim 2, wherein the guidance arrangement moves the laser treatment device with respect to the bed or moves the bed with respect to the laser treatment device.

4. The apparatus of claim 2, wherein both the thermal imaging camera and the laser treatment device are mounted on a single arm which is moveable with respect to the bed or in which the bed is moveable with respect to the single arm or both the bed and the single arm are moveable with respect to each other.

5. The apparatus of claim 2, wherein the thermal imaging camera and the laser treatment device are mounted on separate arms each of which can move with respect to the bed.

6. The apparatus of claim 2, wherein the bed is arranged to support the patient in a vertical, prone or semi-prone position.

7. The apparatus of claim 1, wherein the servomechanism is operable to direct the laser beam at a selected angle and a selected distance with respect to the patient.

8. The apparatus of claim 1, wherein the laser treatment device provides low-level laser treatment (LLLT).

9. The apparatus of claim 8, wherein the laser treatment device comprises two 300 mW 830 nm infrared laser beams.

10. The apparatus of claim 1, wherein the laser treatment device provides laser treatment radiation at a wavelength of 808 nm, 830 nm or 850 nm.

11. The apparatus of claim 1, wherein the thermal imaging camera provides a digital thermal image, and wherein the point or region of thermal anomaly determined by the processor comprises an area in the digital thermal image that is no more than about 0.5° C. warmer than an immediately surrounding area.

12. The apparatus of claim 1, further comprising a timing clock or timer which prevents the laser beam from being directed to a single point on the patient for more than about 6 minutes.

13. An apparatus for the treatment of a soft tissue injury including associated inflammation, comprising:
- an infrared camera or thermal scanner to scan at least a portion of a patient to provide a thermal dataset;
- a processor operable to receive information from the thermal imaging camera and to review the thermal dataset to determine a point or region of thermal anomaly on the patient;
- a laser treatment device to provide a laser beam, wherein the laser treatment device provides laser treatment radiation at a wavelength in the range of 800 nm to 900 nm; and
- a guidance arrangement comprising a servomechanism operable to move the laser treatment device and to direct the laser beam to a desired location, and wherein the guidance arrangement comprises a universal arm operably attached to the laser treatment device to guide the laser beam to the point or region of thermal anomaly on the patient as determined by the processing arrangement, to thereby treat the patient; and wherein guidance of the laser beam to the point or region of thermal anomaly on the patient brings the laser treatment device into contact with the skin of the patient at a force causing skin blanching; and wherein the laser treatment device comprises a force sensor, photosensor or oximeter to generate and provide a signal to the processor when skin blanching has been detected and to cause the processor to halt the guidance arrangement from further movement of the laser treatment device towards the patient once skin blanching has been caused.

* * * * *